United States Patent
Guo et al.

(10) Patent No.: US 12,188,054 B2
(45) Date of Patent: *Jan. 7, 2025

(54) MODIFIED MONOOXYGENASES FOR THE MANUFACTURE OF HYDROXYLATED HYDROCARBONS BASED ON SUBSTITUTION OF AMINO ACIDS BY ALANINE

(71) Applicant: Covestro Intellectual Property GmbH & Co. KG, Leverkusen (DE)

(72) Inventors: Ruijing Guo, Shanghai (CN); Jen-Chieh Lin, Singapur (SG); Sha Tao, Nanjing (CN); Ying Qian, Nanjing (CN); Chenggang Qiu, Nanjing (CN); Kequan Chen, Nanjing (CN); Kang Li, Nanjing (CN)

(73) Assignee: Covestro Deutschland AG, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 17/607,918

(22) PCT Filed: Jun. 18, 2020

(86) PCT No.: PCT/EP2020/066891
§ 371 (c)(1),
(2) Date: Nov. 1, 2021

(87) PCT Pub. No.: WO2020/260118
PCT Pub. Date: Dec. 30, 2020

(65) Prior Publication Data
US 2022/0220455 A1 Jul. 14, 2022

(30) Foreign Application Priority Data

Jun. 27, 2019 (WO) ................ PCT/CN2019/093275
Jun. 27, 2019 (WO) ................ PCT/CN2019/093326
Aug. 16, 2019 (EP) .................................... 19192042
Aug. 16, 2019 (EP) .................................... 19192044

(51) Int. Cl.
*C12N 9/02* (2006.01)
*C12N 1/20* (2006.01)
*C12N 15/00* (2006.01)
*C12P 7/22* (2006.01)
*C12P 17/06* (2006.01)

(52) U.S. Cl.
CPC .......... *C12N 9/0077* (2013.01); *C12N 9/0079* (2013.01); *C12N 15/00* (2013.01); *C12P 7/22* (2013.01); *C12P 17/06* (2013.01); *C12Y 114/15004* (2013.01)

(58) Field of Classification Search
CPC .......... C12N 9/0077; C12N 15/00; C12P 7/22
See application file for complete search history.

(56) References Cited

PUBLICATIONS

Fowler. Cytochrome P450 Monooxygenase can be Redesigned to Catalyse the Regioselective Aromatic Hydroxylation of Diphenylmethane. J. Chem. Soc., Chem. Commun., 1994, pp. 2761-2762.*
Fransceus. J Ind Microbiol Biotechnol. May 2017;44(4-5):687-695.*
Sanavia. Computational and Structural Biotechnology Journal, vol. 18, 2020, pp. 1968-1979.*
Studer. Residue mutations and their impact on protein structure and function: detecting beneficial and pathogenic changes. Biochem. J. (2013) 449, 581-594.*
Unger. J. Biol. Chem. 261, 1158-1163, 1986.*
Liu, L. et al, Cloning, expression, and characterization of a self-sufficient cytochrome P450 monooxygenase from Rhodococcus ruber DSM 44319, Applied Microbiology and Biotechnology, vol. 72, No. 5, Apr. 11, 2006, pp. 876-882, XP037057208.
Tao, S. et al., "Egineering substrate recognition sites of cytochrome P450 monooxygenase CYP116B3 from Rhodococcus ruber for enhanced regiospecific naphtalene hydroxylation", Molecular Catalysis; vol. 493, pp. 1-6; Jul. 7, 2020, XP055729749.
Roberts, G.A. et al., Identification of a New Class of Cytochrome P450 from a *Rhodococcus* sp., Journal of Bacteriology, vol. 184, No. 14, Jul. 2002, pp. 3898-3908.
International Search Report, PCT/EP2020/066891, date of mailing: Oct. 8, 2020, Authorized officer: Ulrike Fuchs.

* cited by examiner

*Primary Examiner* — Yong D Pak
(74) *Attorney, Agent, or Firm* — The Webb Law Firm

(57) ABSTRACT

The present invention relates to novel monooxygenases which are useful in the hydroxylation of aromatic hydrocarbons. They are particularly useful for the production of 1-naththol and 7-hydroxycoumarin from naphthol and 7-Ethoxycoumarin, respectively.

22 Claims, No Drawings
Specification includes a Sequence Listing.

SEQUENCE LISTING

```
<160> NUMBER OF SEQ ID NOS: 4

<210> SEQ ID NO 1
<211> LENGTH: 771
<212> TYPE: PRT
<213> ORGANISM: Rhodococcus ruber

<400> SEQUENCE: 1

Met Ser Ala Ser Val Pro Ala Ser Ala Cys Pro Val Asp His Ala Ala
1               5                   10                  15

Leu Ala Gly Gly Cys Pro Val Ser Thr Asn Ala Ala Phe Asp Pro
                20                  25                  30

Phe Gly Pro Ala Tyr Gln Ala Asp Pro Ala Glu Ser Leu Arg Trp Ser
            35                  40                  45

Arg Asp Glu Glu Pro Val Phe Tyr Ser Pro Gly Leu Gly Tyr Trp Val
    50                  55                  60

Val Thr Arg Tyr Glu Asp Val Lys Ala Val Phe Arg Asp Asn Leu Val
65                  70                  75                  80

Phe Ser Pro Ala Ile Ala Leu Glu Lys Ile Thr Pro Val Ser Glu Glu
                85                  90                  95

Ala Thr Ala Thr Leu Ala Arg Tyr Asp Tyr Ala Met Ala Arg Thr Leu
            100                 105                 110

Val Asn Glu Asp Glu Pro Ala His Met Pro Arg Arg Ala Leu Met
            115                 120                 125

Asp Pro Phe Thr Pro Lys Glu Leu Ala His His Glu Ala Met Val Arg
    130                 135                 140

Arg Leu Thr Arg Glu Tyr Val Asp Arg Phe Val Glu Ser Gly Lys Ala
145                 150                 155                 160

Asp Leu Val Asp Glu Met Leu Trp Glu Val Pro Leu Thr Val Ala Leu
                165                 170                 175

His Phe Leu Gly Val Pro Glu Glu Asp Met Ala Thr Met Arg Lys Tyr
            180                 185                 190

Ser Ile Ala His Thr Val Asn Thr Trp Gly Arg Pro Ala Pro Glu Glu
        195                 200                 205

Gln Val Ala Val Ala Glu Ala Val Gly Arg Phe Trp Gln Tyr Ala Gly
    210                 215                 220

Thr Val Leu Glu Lys Met Arg Gln Asp Pro Ser Gly His Gly Trp Met
225                 230                 235                 240
```

```
Pro Tyr Gly Ile Arg Met Gln Gln Gln Met Pro Asp Val Val Thr Asp
            245                 250                 255
Ser Tyr Leu His Ser Met Met Met Ala Gly Ile Val Ala Ala His Glu
        260                 265                 270
Thr Thr Ala Asn Ala Ser Ala Asn Ala Phe Lys Leu Leu Leu Glu Asn
    275                 280                 285
Arg Pro Val Trp Glu Glu Ile Cys Ala Asp Pro Ser Leu Ile Pro Asn
290                 295                 300
Ala Val Glu Glu Cys Leu Arg His Ser Gly Ser Val Ala Ala Trp Arg
305                 310                 315                 320
Arg Val Ala Thr Thr Asp Thr Arg Ile Gly Asp Val Asp Ile Pro Ala
                325                 330                 335
Gly Ala Lys Leu Leu Val Val Asn Ala Ser Ala Asn His Asp Glu Arg
            340                 345                 350
His Phe Asp Arg Pro Asp Glu Phe Asp Ile Arg Arg Pro Asn Ser Ser
        355                 360                 365
Asp His Leu Thr Phe Gly Tyr Gly Ser His Gln Cys Met Gly Lys Asn
    370                 375                 380
Leu Ala Arg Met Glu Met Gln Ile Phe Leu Glu Glu Leu Thr Thr Arg
385                 390                 395                 400
Leu Pro His Met Glu Leu Val Pro Asp Gln Glu Phe Thr Tyr Leu Pro
                405                 410                 415
Asn Thr Ser Phe Arg Gly Pro Asp His Val Trp Val Gln Trp Asp Pro
            420                 425                 430
Gln Ala Asn Pro Glu Arg Thr Asp Pro Ala Val Leu Gln Arg Gln His
        435                 440                 445
Pro Val Thr Ile Gly Glu Pro Ser Thr Arg Ser Val Ser Arg Thr Val
    450                 455                 460
Thr Val Glu Arg Leu Asp Arg Ile Val Asp Asp Val Leu Arg Val Val
465                 470                 475                 480
Leu Arg Ala Pro Ala Gly Asn Ala Leu Pro Ala Trp Thr Pro Gly Ala
                485                 490                 495
His Ile Asp Val Asp Leu Gly Ala Leu Ser Arg Gln Tyr Ser Leu Cys
            500                 505                 510
Gly Ala Pro Asp Ala Pro Thr Tyr Glu Ile Ala Val Leu Leu Asp Pro
        515                 520                 525
Glu Ser Arg Gly Gly Ser Arg Tyr Val His Glu Gln Leu Arg Val Gly
    530                 535                 540
Gly Ser Leu Arg Ile Arg Gly Pro Arg Asn His Phe Ala Leu Asp Pro
545                 550                 555                 560
Asp Ala Glu His Tyr Val Phe Val Ala Gly Ile Gly Ile Thr Pro
                565                 570                 575
Val Leu Ala Met Ala Asp His Ala Arg Ala Arg Gly Trp Ser Tyr Glu
            580                 585                 590
Leu His Tyr Cys Gly Arg Asn Arg Ser Gly Met Ala Tyr Leu Glu Arg
        595                 600                 605
Val Ala Gly His Gly Asp Arg Ala Ala Leu His Val Ser Ala Glu Gly
    610                 615                 620
Thr Arg Val Asp Leu Ala Ala Leu Leu Ala Thr Pro Val Ser Gly Thr
625                 630                 635                 640
Gln Ile Tyr Ala Cys Gly Pro Gly Arg Leu Leu Ala Gly Leu Glu Asp
                645                 650                 655
Ala Ser Arg His Trp Pro Asp Gly Ala Leu His Val Glu His Phe Thr
```

```
              660                 665                 670
Ser Ser Leu Thr Ala Leu Asp Pro Asp Val Glu His Ala Phe Asp Leu
            675                 680                 685

Asp Leu Arg Asp Ser Gly Leu Thr Val Arg Val Glu Pro Thr Gln Thr
        690                 695                 700

Val Leu Asp Ala Leu Arg Ala Asn Asn Ile Asp Val Pro Ser Asp Cys
705                 710                 715                 720

Glu Glu Gly Leu Cys Gly Ser Cys Glu Val Thr Val Leu Glu Gly Glu
                725                 730                 735

Val Asp His Arg Asp Thr Val Leu Thr Lys Ala Glu Arg Ala Ala Asn
            740                 745                 750

Arg Gln Met Met Thr Cys Cys Ser Arg Ala Cys Gly Asp Arg Leu Thr
        755                 760                 765

Leu Arg Leu
    770

<210> SEQ ID NO 2
<211> LENGTH: 7672
<212> TYPE: DNA
<213> ORGANISM: Artificial Sequence
<220> FEATURE:
<223> OTHER INFORMATION: Expression construct

<400> SEQUENCE: 2
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta atcgggggc tccctttagg     180 gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta taagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg aattaattct tagaaaaact catcgagcat caaatgaaac tgcaatttat    600
tcatatcagg attatcaata ccatattttt gaaaagccg tttctgtaat gaaggagaaa     660
actcaccgag gcagttccat aggatggcaa gatcctggta tcggtctgcg attccgactc    720
gtccaacatc aatacaacct attaatttcc cctcgtcaaa ataaggttat caagtgaga    780 atcaccatg agtgacgact gaatccggtg agaatggcaa agtttatgc atttctttcc      840 agacttgttc aacaggccag ccattacgct cgtcatcaaa atcactcgca tcaaccaaac    900
cgttattcat cgtgattgc gcctgagcga cgaaatac gcgatcgctg ttaaaaggac        960
aattacaaac aggaatcgaa tgcaaccggc gcaggaacac tgccagcgca tcaacaatat   1020
tttcacctga atcaggatat tcttctaata cctggaatgc tgttttcccg gggatcgcag   1080
tggtgagtaa ccatgcatca tcaggagtac ggataaaatg cttgatggtc ggaagaggca   1140
taaattccgt cagccagttt agtctgacca tctcatctgt aacatcattg gcaacgctac   1200
ctttgccatg tttcagaaac aactctggcg catcgggctt cccatacaat cgatagattg   1260
tcgcacctga ttgcccgaca ttatcgcgag cccatttata cccatataaa tcagcatcca   1320
tgttggaatt taatcgcggc ctagagcaag acgtttcccg ttgaatatgg ctcataacac   1380
```

-continued

```
cccttgtatt actgtttatg taagcagaca gttttattgt tcatgaccaa atcccttaa    1440
cgtgagtttt cgttccactg agcgtcagac cccgtagaaa agatcaaagg atcttcttga   1500
gatcctttt  ttctgcgcgt aatctgctgc ttgcaaacaa aaaaaccacc gctaccagcg   1560
gtggtttgtt tgccggatca agagctacca actcttttc cgaaggtaac tggcttcagc    1620
agagcgcaga taccaaatac tgtccttcta gtgtagccgt agttaggcca ccacttcaag   1680
aactctgtag caccgcctac ataccctgct ctgctaatcc tgttaccagt ggctgctgcc   1740
agtggcgata agtcgtgtct taccgggttg gactcaagac gatagttacc ggataaggcg   1800
cagcggtcgg gctgaacggg gggttcgtgc acacagccca gcttggagcg aacgacctac   1860
accgaactga gatacctaca gcgtgagcta tgagaaagcg ccacgcttcc cgaagggaga   1920
aaggcggaca ggtatccggt aagcggcagg gtcggaacag gagagcgcac gagggagctt   1980
ccagggggaa acgcctggta tctttatagt cctgtcgggt ttcgccacct ctgacttgag   2040
cgtcgatttt tgtgatgctc gtcaggggg cggagcctat ggaaaaacgc cagcaacgcg    2100
gccttttac ggttcctggc cttttgctgg ccttttgctc acatgttctt tcctgcgtta    2160
tcccctgatt ctgtggataa ccgtattacc gcctttgagt gagctgatac cgctcgccgc   2220
agccgaacga ccgagcgcag cgagtcagtg agcgaggaag cggaagagcg cctgatgcgg   2280
tattttctcc ttacgcatct gtgcggtatt tcacaccgca tatatggtgc actctcagta   2340
caatctgctc tgatgccgca tagttaagcc agtatacact ccgctatcgc tacgtgactg   2400
ggtcatggct gcgccccgac acccgccaac acccgctgac gcgccctgac gggcttgtct   2460
gctcccggca tccgcttaca gacaagctgt gaccgtctcc gggagctgca tgtgtcagag   2520
gttttcaccg tcatcaccga aacgcgcgag gcagctgcgg taaagctcat cagcgtggtc   2580
gtgaagcgat tcacagatgt ctgcctgttc atccgcgtcc agctcgttga gtttctccag   2640
aagcgttaat gtctggcttc tgataaagcg ggccatgtta agggcggttt tttcctgttt   2700
ggtcactgat gcctccgtgt aagggggatt tctgttcatg ggggtaatga taccgatgaa   2760
acgagagagg atgctcacga tacgggttac tgatgatgaa catgcccggt tactggaacg   2820
ttgtgagggt aaacaactgg cggtatggat gcggcgggac cagagaaaaa tcactcaggg   2880
tcaatgccag cgcttcgtta atacagatgt aggtgttcca cagggtagcc agcagcatcc   2940
tgcgatgcag atccggaaca taatggtgca gggcgctgac ttccgcgttt ccagacttta   3000
cgaaacacgg aaaccgaaga ccattcatgt tgttgctcag gtcgcagacg ttttgcagca   3060
gcagtcgctt cacgttcgct cgcgtatcgg tgattcattc tgctaaccag taaggcaacc   3120
ccgccagcct agccgggtcc tcaacgacag gagcacgatc atgcgcaccc gtggggccgc   3180
catgccggcg ataatggcct gcttctcgcc gaaacgtttg gtggcgggac cagtgacgaa   3240
ggcttgagcg agggcgtgca agattccgaa taccgcaagc gacaggccga tcatcgtcgc   3300
gctccagcga aagcggtcct cgccgaaaat gacccagagc gctgccggca cctgtcctac   3360
gagttgcatg ataaagaaga cagtcataag tgcggcgacg atagtcatgc cccgcgccca   3420
ccggaaggag ctgactgggt tgaaggctct caagggcatc ggtcgagatc ccggtgccta   3480
atgagtgagc taacttacat taattgcgtt gcgctcactg cccgctttcc agtcgggaaa   3540
cctgtcgtgc cagctgcatt aatgaatcgg ccaacgcgcg gggagaggcg gtttgcgtat   3600
tgggcgccag ggtggttttt cttttcacca gtgagacggg caacagctga ttgcccttca   3660
ccgcctggcc ctgagagagt tgcagcaagc ggtccacgct ggtttgcccc agcaggcgaa   3720
aatcctgttt gatggtggtt aacggcggga tataacatga gctgtcttcg gtatcgtcgt   3780
```

```
atcccactac cgagatatcc gcaccaacgc gcagcccgga ctcggtaatg gcgcgcattg    3840
cgcccagcgc catctgatcg ttggcaacca gcatcgcagt gggaacgatg ccctcattca    3900
gcatttgcat ggtttgttga aaaccggaca tggcactcca gtcgccttcc cgttccgcta    3960
tcggctgaat ttgattgcga gtgagatatt tatgccagcc agccgacgc agacgcgccg     4020 agacagaact taatgggccc gctaacagcg cgatttgctg gtgacccaat gcgaccagat    4080
gctccacgcc cagtcgcgta ccgtcttcat gggagaaaat aatactgttg atgggtgtct    4140
ggtcagagac atcaagaaat aacgccggaa cattagtgca ggcagcttcc acagcaatgg    4200
catcctggtc atccagcgga tagttaatga tcagcccact gacgcgttgc gcgagaagat    4260
tgtgcaccgc cgctttacag gcttcgacgc cgcttcgttc taccatcgac accaccacgc    4320
tggcacccag ttgatcggcg cgagatttaa tcgccgcgac aatttgcgac ggcgcgtgca    4380
gggccagact ggaggtggca acgccaatca gcaacgactg tttgcccgcc agttgttgtg    4440
ccacgcggtt gggaatgtaa ttcagctccg ccatcgccgc ttccactttt tcccgcgttt    4500
tcgcagaaac gtggctggcc tggttcacca cgcgggaaac ggtctgataa gagacaccgg    4560
catactctgc gacatcgtat aacgttactg gtttcacatt caccaccctg aattgactct    4620
cttccgggcg ctatcatgcc ataccgcgaa aggttttgcg ccattcgatg gtgtccggga    4680
tctcgacgct ctcccttatg cgactcctgc attaggaagc agcccagtag taggttgagg    4740
ccgttgagca ccgccgccgc aaggaatggt gcatgcaagg agatggcgcc caacagtccc    4800
ccggccacgg ggcctgccac catacccacg ccgaaacaag cgctcatgag cccgaagtgg    4860
cgagcccgat cttccccatc ggtgatgtcg gcgatatagg cgccagcaac cgcacctgtg    4920
gcgccggtga tgccggccac gatgcgtccg gcgtagagga tcgagatctc gatcccgcga    4980
aattaatacg actcactata ggggaattgt gagcggataa caattcccct ctagaaataa    5040
ttttgtttaa ctttaagaag gagatatacc atgggcagca gccatcatca tcatcatcac    5100
agcagcggcc tggtgccgcg cggcagccat atggctagca tgactggtgg acagcaaatg    5160
ggtcgcggat ccgaattcat gagtgcatca gttccggcgt cggcgtgtcc cgtcgatcac    5220
gcggccctgg ccgcggctg tccggtgtcg acgaacgccg cggcgttcga tccgttcggg    5280
cccgcgtacc aggccgatcc ggccgagtcg ctgcgctggt cccgcgacga ggagccggtg    5340
ttctacagcc ccgaactcgg ctactgggtg gtcaccgct acgaggatgt gaaggcggtg    5400
ttccgcgaca acctcgtgtt ctcaccggcc atcgccctcg agaagatcac cccggtctcc    5460
gaggaggcca ccgccaccct cgcccgctac gactacgcca tggcccggac cctcgtgaac    5520
gaggacgagc ccgcccacat gccgcgccgc cgcgcactca tggacccgtt caccccgaag    5580
gaactggcgc accacgaggc gatggtgcga cggctcacgc gcgaatacgt cgaccgcttc    5640
gtcgaatccg gcaaggccga cctggtggac gagatgctgt gggaggtacc gctcaccgtc    5700
gccctgcact tcctcggcgt gccggaggag gacatggcga cgatgcgcaa gtactcgatc    5760
gcccacaccg tgaacacctg ggccgccccc gcgcccgagg agcaggtcgc cgtcgccgag    5820
gcggtcggca ggttctggca gtacgcgggc acggtgctcg agaagatgcg ccaggacccc    5880
tcggggcacg gctggatgcc ctacgggatc cgcatgcagc agcagatgcc ggacgtcgtc    5940
accgactcct acctgcactc gatgatgatg gccggcatcg tcgccgcgca cgagaccacg    6000
gccaacgcgt ccgcgaacgc gttcaagctg ctgctcgaga accgcccggt gtgggaggag    6060
atctgcgcgg atccgtcgct gatccccaac gccgtcgagg agtgcctgcg ccactcggga    6120
```

```
tcggtcgcgg cgtggcgacg ggtggccacc accgacaccc gcatcggcga cgtcgacatc    6180
cccgccggcg caaagctgct cgtcgtcaac gcctccgcca accatgacga gcggcacttc    6240
gaccgtcccg acgagttcga catccggcgc ccgaactcga gcgaccacct caccttcggg    6300
tacggcagcc atcagtgcat gggcaagaac ctggcccgca tggagatgca gatcttcctc    6360
gaggaactga ccacgcggct tccccacatg gaactcgtac ccgatcagga gttcacctac    6420
ctgccgaaca cctcgttccg cggtcccgat cacgtgtggg tgcagtggga tccgcaggcg    6480
aaccccgagc gcaccgaccc ggccgtgctg caacggcagc atcccgtcac catcggcgag    6540
ccctccaccc ggtcggtgtc acgcaccgtc accgtcgagc gcctggaccg gatcgtcgac    6600
gacgtgctgc gcgtcgtcct acgggctcct gcaggaaatg cgttgcccgc gtggactcct    6660
ggcgcccaca tcgatgtcga cctcggtgcg ctgtcgcggc agtactccct gtgcggtgcg    6720
cccgacgcgc ccacctacga gatcgccgtt ctgctggacc ccgagagccg cggtggctcg    6780
cgctacgtcc acgaacagct ccgggtgggg ggatcgctcc ggattcgcgg gccccggaac    6840
cacttcgcgc tcgaccccga cgccgagcac tacgtgttcg tggccggcgg catcggcatc    6900
accccgtcc tggccatggc cgaccacgcc cgcgcccggg ggtggagcta cgaactgcac    6960
tactgcggcc ggaaccgttc cgggatggcc tatctcgagc gggtcgccgg gcacggggac    7020
cgcgccgccc tgcacgtctc ggcggaaggc accgggtcg acctcgccgc cctcctcgcg    7080
acgccggtgt ccggcaccca gatctacgcg tgcgggcccg gacggctgct cgccggactc    7140
gaggacgcga gccggcactg gcccgacggt gcgctgcacg tcgagcactt cacctcgtcc    7200
ctcacggcac tcgacccgga cgtcgagcac gccttcgacc tcgacctgcg cgactcggga    7260
ctcaccgtgc gggtcgagcc cacccagacc gtcctcgacg cgttgcgcgc caacaacatc    7320
gacgtgccca gcgactgcga ggaaggcctc tgcggctcct gcgaggtcac cgtcctcgaa    7380
ggcgaggtcg accaccgcga caccgtgctc accaaggccg agcgggcggc gaaccggcag    7440
atgatgacct gctgctcgcg tgcctgcggc gaccgactga ccctccgact ctgaaagctt    7500
gcggccgcac tcgagcacca ccaccaccac cactgagatc cggctgctaa caaagcccga    7560
aaggaagctg agttggctgc tgccaccgct gagcaataac tagcataacc ccttggggcc    7620
tctaaacggg tcttgagggg ttttttgctg aaaggaggaa ctatatccgg at            7672

<210> SEQ ID NO 3
<211> LENGTH: 31
<212> TYPE: DNA
<213> ORGANISM: Artificial Sequence
<220> FEATURE:
<223> OTHER INFORMATION: PCR primer

<400> SEQUENCE: 3
ctggaattca tgagtgcatc agttccggcg t                                    31

<210> SEQ ID NO 4
<211> LENGTH: 27
<212> TYPE: DNA
<213> ORGANISM: Artificial Sequence
<220> FEATURE:
<223> OTHER INFORMATION: PCR primer

<400> SEQUENCE: 4
catcaagctt tcagagtcgc agggcca                                         27
```

MODIFIED MONOOXYGENASES FOR THE MANUFACTURE OF HYDROXYLATED HYDROCARBONS BASED ON SUBSTITUTION OF AMINO ACIDS BY ALANINE

CROSS-REFERENCE TO RELATED APPLICATION

This application is a national stage application under 35 U.S.C. § 371 of PCT/EP2020/066891, filed Jun. 18, 2020, which claims the benefit of European Application No. 19192044.6, filed Aug. 16, 2019, European Application No. 19192042.0, filed Aug. 16, 2019, International Application No. PCT/CN2019/093326, filed Jun. 27, 2019, and International Application No. PCT/CN2019/093275, filed Jun. 27, 2019, each of which is incorporated herein by reference.

FIELD

The present invention relates to novel monooxygenases which are useful in the hydroxylation of aromatic hydrocarbons. They are particularly useful for the production of 1-naththol and 7-hydroxycoumarin from naphthalene and 7-ethoxycoumarin, respectively.

BACKGROUND

Hydroxylated hydrocarbons, particularly 1-naththol and 7-hydroxycoumarin, are important raw materials in the chemical industry. Presently, said compounds are produced by purely chemical processes. The currently used chemical methods of producing 1-naphthol are mainly divided into three types. The most widely used method in large-scale production is based hydrogenation, oxidation and dehydrogenation of naphthalene. This method is characterized by high quality and continuous production, but low yield. Moreover, current methods of manufacturing naphthols require acids, bases and metal catalysts. These compounds may be expensive or may cause environmental problems if not disposed of properly. Proper disposal may be an additional cost factor.

Biotechnological methods have become more popular for the synthesis of chemical compounds. Generally, such methods are characterized by mild reaction conditions, thus saving energy, and high specificity so that few undesired side products are formed. A P450 monooxygenase capable of introducing hydroxyl groups into a variety of aromatic hydrocarbons has been isolated from *Rhodococcus ruber* (Liu et al., 2006, Appl. Microbiol. Biotechnol. 72: 876-882). In principle, this enzyme opens the route to biotechnological methods for manufacturing hydroxylated aromatic hydrocarbons. However, the wild-type enzyme has a low catalytic activity which is not sufficient for an economically viable production process.

SUMMARY

The above-described problems are solved by the embodiments defined in the claims and in the description below.

DETAILED DESCRIPTION

In a first embodiment, the present invention relates to a modified P450 monooxygenase, wherein at least one amino acid selected from the group consisting of leucine 87, glutamic acid 88, lysine 89, isoleucine 90, threonine 91, proline 92, valine 93, serine 94, glutamic acid 95, glutamic acid 96, threonine 98, threonine 100, leucine 101, arginine 103, tyrosine 104, aspartic acid 105, histidine 196, threonine 197, valine 198, asparagine 199, threonine 200, tryptophan 201, glycine 202, arginine 203, proline 204, proline 206, glutamic acid 207, glutamic acid 208, glutamine 209 and valine 210 is substituted by alanine, wherein said functional mutation leads to an improved reactivity on hydroxylation of aromatic hydrocarbons.

SEQ ID NO. 1 defines the amino acid sequence of a P450 monooxygenase originally derived from *Rhodococcus ruber*. A "modified P450 monooxygenase" has an amino acid sequence which differs by at least one of the substitutions defined above from the amino acid sequence defined in SEQ ID NO. 1.

In addition to the sequence modifications set forth above and below in this application, the amino acid sequence of the modified P450 monooxygenase of the present invention may have further differences to the amino acid sequence of the wild-type enzyme as defined by SEQ ID NO. 1 provided that these sequence differences do not affect its function, i.e. the improved reactivity on hydroxylation of aromatic carbons. It is well known to the person skilled in the art that not all parts of the amino acid sequence of an enzyme are equally important. Sequence regions which are not part of the aforementioned regions may in many cases be altered or even deleted without impairing the enzymatic activity of the protein.

Therefore, the present invention also relates to proteins having at least 90%, more preferably at least 95% and most preferably at least 98% sequence identity to the amino acid sequence defined by SEQ ID NO. 1, provided that such proteins still have an improved reactivity on the hydroxylation of aromatic hydrocarbons.

The person skilled in the art is aware that additions or deletions of amino acids from SEQ ID NO. 1 may shift the particular amino acids positions recited in this application. Therefore, any amino acid position referred to in this application based on the wild-type sequence must be understood as referring to the homologous amino acid position in a protein derived from SEQ ID NO. 1 by deleting or adding amino acids.

Variants of SEQ ID NO. 1 having the degrees of sequence identity set forth above are preferably derived from SEQ ID NO. 1 only by conservative substitutions of amino acids. A "conservative substitution" is a substitution on one amino acid by a different amino acid with similar properties. Preferably, it is an exchange of an amino acid with a non-polar side chain for another amino acid with a non-polar side chain, an exchange of an amino acid with an acidic side chain for another amino acid with an acidic side chain, an amino acid with a basic side chain for another amino acid with a basic side chain or an exchange of an amino acid with a polar side chain for another amino acid with a polar side chain. Because the properties of the side chains in conservative substitutions do not change much, the overall structure of the resulting protein will not be severely affected.

Variants of SEQ ID NO. 1 derived from this sequence by addition of amino acids and having the degrees of sequence identity set forth above are, preferably, derived from SEQ ID NO. 1 by addition of up to 35, more preferably up to 20 and most preferably up to 10 amino acids at the C-terminus and/or the N-terminus. Typical additions to a protein are additions of amino acid sequences which make the purification of the expressed protein easier. One particularly preferred modification is the addition of several histidines, a so-called "his-tag". Also preferred is the addition of peptide linkers.

Variants of SEQ ID NO. 1 derived from this sequence by deletion of amino acids and having the degrees of sequence identity set forth above are, preferably, derived from SEQ ID NO. 1 by deletion of up to 35, more preferably up to 20 and most preferably up to 10 amino acids at the C-terminus and/or the N-terminus.

"Polar amino acids" or "amino acids with polar side chains" as understood by the present application are glycine, serine, threonine, cysteine, asparagine, glutamine, tryptophan and tyrosine.

"Non-polar amino acids" "amino acids with polar side chains" as understood by the present application are alanine, valine, leucine, iso-leucine, phenylalanine, proline, and methionine.

Amino acids with acidic side chains as understood by the present application are aspartate and glutamic acid.

Amino acids with basic side chains as understood by the present application are lysine, arginine and histidine.

In a preferred embodiment of the present invention, at least one of the polar amino acids belonging to the group consisting of glutamic acid 88, lysine 89, threonine 100, leucine 101, arginine 103, asparagine 199, arginine 203, proline 204 and glutamine 209 is substituted by alanine.

If the transformation of naphthalene to 1-naphthol is intended, in the modified P450 monooxygenase according to the present invention at least one of the polar amino acids belonging to the group consisting of glutamic acid 88, asparagine 199, arginine 203 and glutamine 209 is substituted by alanine.

If the transformation of 7-Ethoxycoumarin to hydroxycoumarin is intended, in the modified P450 monooxygenase according to the present invention at least one of the polar amino acids belonging to the group consisting of glutamic acid 88, lysine 89, leucine 101, arginine 103, asparagine 199, arginine 203, proline 204 and glutamine 209 is substituted by alanine.

Since the substitutions of glutamic acid 88, asparagine 199, arginine 203 and glutamine 209 work well for both transformations, in a particularly preferred modified P450 monooxygenase at least one of the amino acids selected from this group is exchanged for a non-polar amino acid.

In a particularly preferred modified monooxygenase according to the present invention at least two of the above-mentioned polar amino acids are by alanine. Preferred combinations are the combination of glutamic acid 88 and asparagine 199, the combination of glutamic acid 88 and arginine 203, the combination of glutamic acid 88 and glutamine 209, the combination of asparagine 199 and arginine 203, the combination of asparagine 199 and glutamine 209 or the combination of arginine 203 and glutamine 209.

In another particularly preferred modified monooxygenase according to the present invention at least three of the above-mentioned polar amino acids are exchanged for non-polar ones. Preferred combinations are the combination of glutamic acid 88, asparagine 199 and arginine 203, the combination of asparagine 199, arginine 203 and glutamine 209, the combination of glutamic acid 88, arginine 203 and glutamine 209 or the combination of glutamic acid 88, asparagine 199 and glutamine 209.

In another particularly preferred modified monooxygenase according to the present invention glutamic acid 88, asparagine 199, arginine 203 and glutamine 209 are exchanged for non-polar amino acids.

Substitution at Position 209

In one preferred embodiment of the present invention, the modified P450 monooxygenase has an alanine at position 209.

Preferably, additionally at least one of the other amino acids selected from the group consisting of leucine 87, glutamic acid 88, lysine 89, isoleucine 90, threonine 91, proline 92, valine 93, serine 94, glutamic acid 95, glutamic acid 96, threonine 98, threonine 100, leucine 101, arginine 103, tyrosine 104, aspartic acid 105, histidine 196, threonine 197, valine 198, asparagine 199, threonine 200, tryptophan 201, glycine 202, arginine 203, proline 204, proline 206, glutamic acid 207, glutamic acid 208, and valine 210 is substituted by alanine.

In one particularly preferred embodiment of the present invention, in addition to the substitution of glutamine at position 209 by alanine, glutamic acid at position 88 is substituted by an amino acid selected from the group consisting of alanine, serine, histidine, threonine, cysteine, methionine and asparagine. More preferably, glutamic acid at position 88 is substituted by an amino acid selected from the group consisting of alanine, serine, histidine, threonine, cysteine and methionine. With these substitutions, the catalytic activity of the enzyme with naphthalene as wells as 7-ethoxycoumarin is increased. Most preferably glutamic acid at position 88 is substituted by an amino acid selected from the group consisting of alanine, cysteine and methionine.

In another particularly preferred embodiment of the present invention, in addition to the substitution of glutamine at position 209 by alanine, asparagine at position 199 of the P450 monooxygenase defined by SEQ ID NO: 1 is substituted by an amino acid selected from the group consisting of glutamine, isoleucine, leucine, phenylalanine, histidine, methionine, arginine, serine, threonine, tyrosine, tryptophan, alanine, valine and lysine. Preferably, the modified P450 monooxygenase carries a glutamine at position 199.

In this embodiment, it is particularly preferred that in addition to the substitution of glutamine at position 209 by alanine, both glutamic acid at position 88 and asparagine at position 199 are substituted as defined above.

A particularly preferred modified P450 monooxygenase carries the following substitutions:
(i) an amino acid selected from the group consisting of alanine, cysteine and methionine at position 88;
(ii) an amino acid selected from the group consisting of glutamine, isoleucine, leucine phenylalanine, histidine, methionine, arginine, serine, threonine, tyrosine, tryptophan, alanine, valine and lysine at position 199, preferably glutamine; and
(iii) alanine at position 209.

Substitution at Position 88

In one preferred embodiment of the present invention, the modified P450 monooxygenase has an alanine at position 88.

Preferably, additionally at least one of the other amino acids selected from the group consisting of leucine 87, lysine 89, isoleucine 90, threonine 91, proline 92, valine 93, serine 94, glutamic acid 95, glutamic acid 96, threonine 98, threonine 100, leucine 101, arginine 103, tyrosine 104, aspartic acid 105, histidine 196, threonine 197, valine 198, asparagine 199, threonine 200, tryptophan 201, glycine 202, arginine 203, proline 204, proline 206, glutamic acid 207, glutamic acid 208, glutamine 209 and valine 210 is substituted by alanine.

In one particularly preferred embodiment of the present invention, in addition to the substitution of glutamic acid at position 88 by alanine, asparagine at position 199 of the P450 monooxygenase defined by SEQ ID NO: 1 is substituted by an amino acid selected from the group consisting of glutamine, isoleucine, leucine phenylalanine, histidine, methionine, arginine, serine, threonine, tyrosine, tryptophan, alanine, valine and lysine. Preferably, the modified P450 monooxygenase carries a glutamine at position 199.

The term "reactivity with hydrocarbons" refers to the enzyme's ability to introduce an hydroxyl group into a hydrocarbon compound selected from the group consisting of naphthalene, 7-ethoxycoumarin, acenaphthene, fluorine, indene, toluene, ethylbenzene and m-xylene. Preferably, the modified P450 monooxygenase of the present invention has an improved reactivity on hydroxylation of naphthalene and/or 7-ethoxycoumarin.

The reaction hydroxylation of the aforementioned substrates with the P450 monooxygenase of the present invention can be found below:

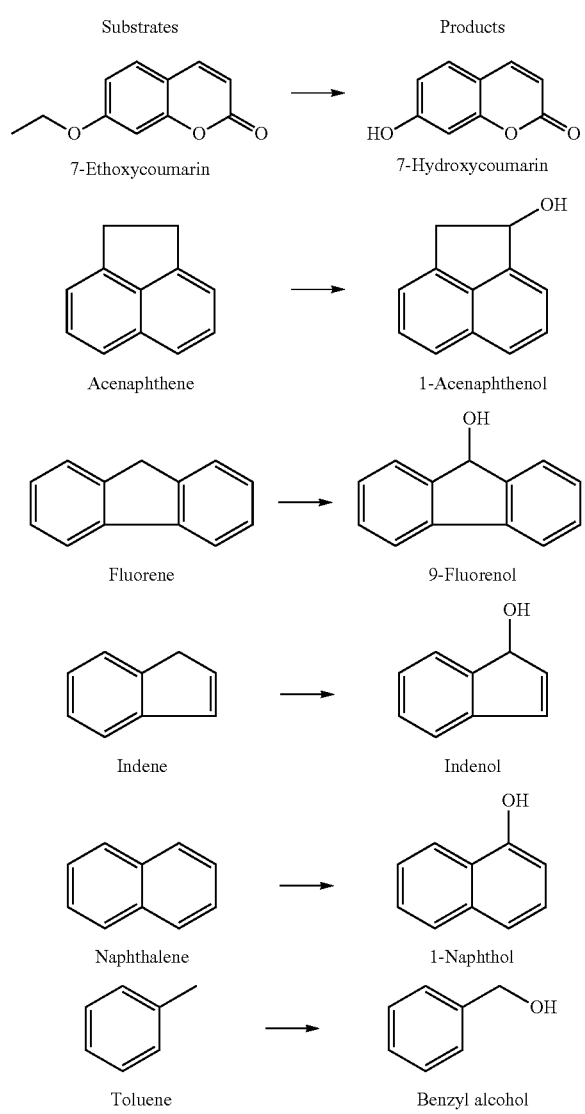

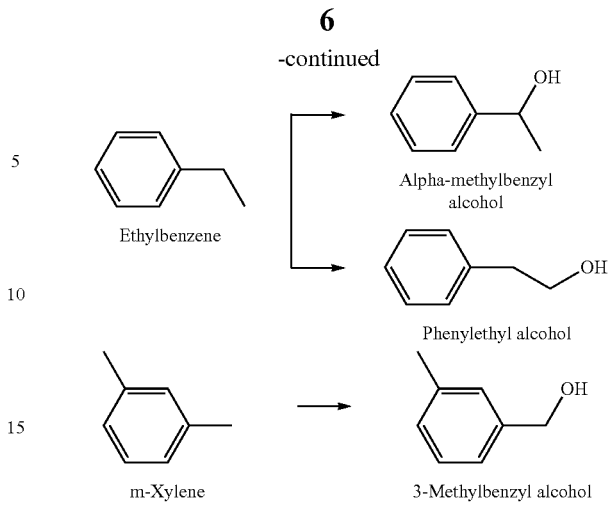

The reactivity on hydroxylation of aromatic carbons is, preferably, determined in phosphate-buffered saline solution (PBS) with 0.15 g/l of the hydrocarbon to be tested. The hydrocarbon is, preferably, taken from a 3 g/l stock solution in DMSO. The preferred incubation time at 30° C. is 2 hours. The products are then extracted with methyl-tert butyl ether and analyzed by HPLC, preferably using a C18 reverse-phase column. An enzyme shows "improved reactivity" towards the hydrocarbon in question of its specific activity in the above-described assay is higher than that of the wild-type enzyme defined by SEQ ID NO. 1. Preferably, the specific activity is determined using equal concentrations of a purified enzyme. However, a whole-cell assay as described in the examples may also be used.

In another embodiment the present invention relates to nucleic acid sequence encoding any of the modified P450 monooxygenase defined above. The invention also relates nucleic acid sequences having a complementary sequence to the aforementioned nucleic acid sequence.

In yet another embodiment, the present invention relates to an expression construct, comprising the nucleic acid sequence of claim 5 as defined above under the genetic control of a regulatory nucleic acid sequence.

The term "expression construct" is well known to the person skilled in the art. An "expression construct" is a nucleic acid molecule comprising a protein coding region and a regulatory sequence which enables the transcription of the protein coding region. Suitable regulatory sequences depend on the host cell which is intended to be used for the recombinant expression of the protein. The person skilled in the art is able to select suitable regulatory regions based on his common knowledge about transcription processes in the selected host cell. A preferred expression construct for the recombinant expression of a modified P450 monooxygenase according to the present invention in E. coli has a nucleic acid sequence as defined by SEQ ID NO. 2

In yet another embodiment, the present invention relates to a vector, comprising the nucleic acid as defined above or the expression construct as defined above.

The term "vector" is well known to the person skilled in the art. It is a nucleic acid sequence which can be replicated in a host cell. Hence, it must comprise all genetic elements which are required for successful replication in the selected host cell. The person skilled in the art knows which vectors to use for a specific host cell.

In yet another embodiment, the present invention relates to a microorganism comprising the nucleic acid as defined above or the expression construct as defined above or the vector as defined above.

In principle, any microorganism which allows the recombinant expression of transgenes may be used. Thus, the suitable microorganism is one, for which regulatory elements as defined above are known and for which vectors as defined above may be constructed. Preferably, the microorganism is a prokaryote, more preferably a bacterium. Preferred bacteria belong to the genera *Rhodococcus* or *Escherichia*. A preferred yeast is *Pichia pastoris*. The microorganism is, most preferably, *E. coli, R. ruber* or *Pichia pastoris*.

In yet another embodiment, the present invention relates to a method for producing the modified p450 monooxygenase as defined above in this application comprising the step of incubating the recombinant microorganism as defined above under conditions suitable for the expression of the monooxygenase.

The person skilled in the art knows that different microorganisms have different requirements with regard to the composition of the medium, energy and carbon sources as well as temperature and oxygen supply. He is well able to select suitable conditions based on his knowledge of microbial physiology. If an inducible promotor is used as regulatory element in the expression construct, the person skilled in the art knows the conditions required for the induction of translation.

In yet another embodiment, the present invention relates to a method for the hydroxylation of an aromatic hydrocarbon, comprising the step of a1) having at least one of the modified P450 monooxygenases according to the present invention mixed and reacted with said aromatic hydrocarbon and having said aromatic hydrocarbon thus hydroxylated; or a2) having at least one of the recombinant microorganisms as defined above mixed and reacted with said aromatic hydrocarbon.

The person skilled in the art is able to find suitable reaction conditions by simple experiments. The preferred reaction temperature is 30° C. The preferred pH is 7.4. Preferably, the reaction takes place in the presence of potassium ions (25 mM). The preferred substrate concentration is 0.12 g/L. If whole bacterial cells are used (embodiment a2), the $OD_{600}$ should be 30. The person skilled in the art is well aware that the enzyme retains at least some activity in conditions which deviate in one or more parameters from the conditions given above. Hence, the method of the present invention is not limited to those parameters and the particular parameters disclosed above provide only one of several embodiments of the invention. Using the methods disclosed in the present application, the person skilled in the art can easily test the enzyme's activity under different reaction conditions.

If the method according to a2) is used it is preferred that the microorganism has been incubated under conditions suitable for the expression of the modified P450 monooxygenase before mixing it with said aromatic hydrocarbon. It is also preferred to wash this microorganism in a suitable buffer before mixing it with aromatic hydrocarbon in order to limit the presence of undesired side products.

All definitions pertaining to the modified P450 monooxygenases of the present invention, suitable hydrocarbons and host cells given further above in this application also apply to this embodiment.

In yet another embodiment, the present invention relates to the use of the modified P450 monooxygenase according to the present invention for the hydroxylation of an aromatic carbon.

All definitions given above also apply to this embodiment.

The following examples are only intended to illustrate the invention. They shall not limit the scope of the claims in any way.

EXAMPLES

Construction of Nucleic Acids Encoding Modified P450 Monooxygenases

A full-length gene encoding P450 protein was synthesized and amplified by PCR using the following primers: 5-ctg-GAATTCATGAGTGCATCAGTTCCGGCGT-3 (SEQ ID NO: 3) and 5-catcAAGCTTTCAGAGTCGCAGGGCCA-3 (SEQ ID NO: 4). The EcoRI and HindIII restriction endonuclease sites in the primer sequences are underlined. The PCR product was isolated and digested with EcoRI and HindIII restriction endonucleases, cloned into the pET28a (+) vector, and expressed in *E. coli* BL21(DE3) cells. The sequence of the insert DNA was subsequently confirmed by sequencing.

Mutagenesis was performed as generally known in the art by designing suitable primers and conducting whole plasmid PCR. Thereafter, the original plasmid was digested by DpnI.

Recombinant Expression of Modified P450 Monooxygenases

*E. coli* BL21 (DE3) containing the expression construct was grown in 100 mL Luria-Bertani medium, supplemented with 50 μg ml$^{-1}$ kanamycin, at 37° C. and 120 rpm. Expression was induced with 0.25 mM isopropyl-β-D-thiogalactopyranoside (IPTG) and cells were incubated for 24 h at 18° C. Cells were harvested by centrifugation (~10,000×g), washed with phosphate-buffered saline (PBS) and resuspended into PBS. The cell final concentration was adjusted to $OD_{600}$ 20 before the reaction.

Assessment of the Activity of Recombinant P450 Monooxygenases

The whole-cell reaction was initiated by adding 0.15 g/L PAH from a 3 g/L stock in DMSO to 2 mL working volume in a 10 mL vial. After 2 h, the products were extracted with 2 mL methyl tert-butyl ether (MTBE) after vigorous vortexing for 5 min. After centrifugation, the organic phase was transferred to a fresh glass tube and evaporated to dryness. The remaining residue was resolubilized with methanol. Samples were quantified by HPLC using an Alltech series 1500 instrument equipped with a prevail C18 reverse-phase column maintained at 25° C. For detection, 50% methanol was applied as the mobile phase at a flow rate of 1.0 mL min'. Products were detected by monitoring the absorbance at 272 nm.

TABLE 1 modified P450 monooxygenases and their activities

| Mutants | 1-Naphthol production (mg · L$^{-1}$ · h$^{-1}$) | 7- Hydroxycoumarin production (mg · L$^{-1}$ · h$^{-1}$) |
|---|---|---|
| Wild-type | 0.51 ± 0.05 | 46.98 ± 3.40 |
| L87A | 0.23 ± 0.05 | 48.44 ± 1.78 |
| E88A | 0.99 ± 0.04 | 153.98 ± 1.14 |
| K89A | 0.55 ± 0.02 | 96.31 ± 4.72 |
| I90A | 0.65 ± 0.08 | 58.31 ± 3.07 |

TABLE 1-continued modified P450 monooxygenases and their activities

| Mutants | 1-Naphthol production (mg·L⁻¹·h⁻¹) | 7-Hydroxycoumarin production (mg·L⁻¹·h⁻¹) |
|---|---|---|
| T91A | 0.54 ± 0.12 | 44.98 ± 4.16 |
| P92A | 0.49 ± 0.09 | 49.02 ± 3.07 |
| V93A | 0.20 ± 0.10 | 28.71 ± 4.16 |
| S94A | 0.52 ± 0.05 | 48.14 ± 3.18 |
| E95A | 0.82 ± 0.11 | 62.42 ± 0.46 |
| E96A | 0.56 ± 0.06 | 71.52 ± 4.46 |
| T98A | 0.26 ± 0.05 | 39.84 ± 2.37 |
| T100A | 0.65 ± 0.09 | 86.75 ± 4.00 |
| L101A | 0.68 ± 0.03 | 120.58 ± 3.78 |
| R103A | 0.45 ± 0.10 | 76.82 ± 4.29 |
| Y104A | 0.19 ± 0.01 | 35.74 ± 2.96 |
| D105A | 0.41 ± 0.13 | 36.46 ± 4.14 |
| H196A | 0.54 ± 0.05 | 46.16 ± 3.96 |
| T197A | 0.71 ± 0.08 | 48.43 ± 2.91 |
| V198A | 0.08 ± 0.04 | 38.70 ± 0.57 |
| N199A | 1.73 ± 0.01 | 134.04 ± 2.54 |
| T200A | 0.44 ± 0.04 | 46.72 ± 3.15 |
| W201A | 0.35 ± 0.12 | 33.79 ± 2.38 |
| G202A | 0.37 ± 0.10 | 35.65 ± 1.12 |
| R203A | 1.28 ± 0.04 | 144.63 ± 5.60 |
| P204A | 0.66 ± 0.07 | 182.97 ± 9.32 |
| P206A | 0.29 ± 0.13 | 39.31 ± 0.85 |
| E207A | 0.58 ± 0.05 | 62.62 ± 5.67 |
| E28A | 0.37 ± 0.04 | 24.84 ± 1.56 |
| Q209A | 1.90 ± 0.07 | 225.27 ± 3.04 |
| V210A | 0.49 ± 0.02 | 43.92 ± 2.93 |

The invention claimed is:

1. A modified P450 monooxygenase having an amino acid sequence with at least 95% sequence identity with SEQ ID NO.: 1, wherein at least one amino acid of SEQ ID NO.: 1 selected from the group consisting of leucine 87, glutamic acid 88, lysine 89, isoleucine 90, threonine 91, proline 92, valine 93, serine 94, glutamic acid 96, threonine 98, threonine 100, leucine 101, arginine 103, tyrosine 104, aspartic acid 105, histidine 196, threonine 197, valine 198, asparagine 199, threonine 200, tryptophan 201, glycine 202, arginine 203, proline 204, proline 206, glutamic acid 207, glutamic acid 208, glutamine 209, valine 210, and combinations thereof is substituted by alanine, leading to an improved reactivity on hydroxylation of aromatic hydrocarbons as compared to a non-modified P450 oxygenase.

2. The modified P450 monooxygenase according to claim 1, wherein glutamine at position 209 is substituted by alanine.

3. The modified P450 monooxygenase according to claim 2, further comprising at least one of the following substitutions:
   a) substitution of glutamic acid at position 88 by an amino acid selected from the group consisting of alanine, serine, histidine, threonine, cysteine, methionine, and asparagine; and/or
   b) substitution of asparagine at position 199 by an amino acid selected from the group consisting of glutamine, isoleucine, leucine, phenylalanine, histidine, methionine, arginine, serine, threonine, tyrosine, tryptophan, alanine, valine, and lysine.

4. The modified P450 monooxygenase according to claim 1, wherein glutamic acid at position 88 is substituted by alanine.

5. The modified P450 monooxygenase according to claim 4, further comprising at least one of the following substitutions:
   a) substitution of glutamic acid at position 199 by an amino acid selected from the group consisting of glutamine, isoleucine, leucine, phenylalanine, histidine, methionine, arginine, serine, threonine, tyrosine, tryptophan, alanine, valine, and lysine; and/or
   b) substitution of glutamine at position 209 by alanine.

6. The modified P450 monooxygenase according to claim 1, having an addition of up to 35 amino acids at the N-terminus and/or the C-terminus.

7. The modified P450 monooxygenase according to claim 1, having a deletion of up to 35 amino acids at the N-terminus and/or the C-terminus.

8. The modified P450 monooxygenase according to claim 1, leading to an increased activity on at least one hydrocarbon selected from the group consisting of naphthalene, 7-ethoxy-hydroxycoumarin, acenaphthene, florene, indene, methylbenzene, and ethylbenzene.

9. A nucleic acid sequence encoding any of the modified P450 monooxygenase according to claim 1 and its complementary nucleic acid sequence.

10. An expression construct, comprising the nucleic acid sequence of claim 9 under the genetic control of a regulatory nucleic acid sequence.

11. A vector, comprising the nucleic acid sequence of claim 9.

12. A microorganism comprising the nucleic acid of claim 9.

13. The microorganism according to claim 12, wherein the microorganism is-belongs to the genus *Rhodococcus* or *Escherichia*.

14. A method for producing the modified p450 monooxygenase of claim 1 comprising: incubating a recombinant microorganism comprising a nucleic acid encoding the modified p450 monooxygenase under conditions suitable for the expression of the modified p450 monooxygenase.

15. A method for the hydroxylation of an aromatic hydrocarbon, comprising:
   mixing at least one of the modified P450 monooxygenases according to claim 1 with said aromatic hydrocarbon under conditions to hydroxylate said aromatic hydrocarbon.

16. The method according to claim 15, wherein the aromatic hydrocarbon is selected from the group consisting of naphthalene, 7-ethoxy-hydroxycoumarin, acenaphthene, florene, indene, methylbenzene, ethylbenzene, and mixtures thereof.

17. The method according to claim 15, wherein the aromatic hydrocarbon is hydroxylated to form a hydroxylated aromatic hydrocarbon selected from the group consisting of 1-naphthol, 7-hydroxycoumarin, 1-acenaphthylene, 9-benflumetol, indenol, benzyl alcohol, 3-methylbenzyl alcohol, and mixtures thereof.

18. The modified p450 monooxygenase according to claim 1, wherein the at least one amino acid is selected from the group consisting of glutamic acid 88, lysine 89, threonine 100, leucine 101, arginine 103, asparagine 199, arginine 203, proline 204, glutamine 209, and combinations thereof.

19. The microorganism of claim 12, comprising an expression construct and/or a vector comprising the nucleic acid.

20. The method according to claim 15, wherein mixing comprises combining a recombinant microorganism with the aromatic hydrocarbon, said recombinant microorganism comprising a nucleic acid encoding the modified p450 monooxygenase.

21. The modified P450 monooxygenase according to claim 2, further comprising at least one amino acid selected from the group consisting of leucine 87, glutamic acid 88, lysine 89, isoleucine 90, threonine 91, proline 92, valine 93, serine 94, glutamic acid 96, threonine 98, threonine 100, leucine 101, arginine 103, tyrosine 104, aspartic acid 105, histidine 196, threonine 197, valine 198, asparagine 199, threonine 200, tryptophan 201, glycine 202, arginine 203, proline 204, proline 206, glutamic acid 207, glutamic acid 208, valine 210 and combinations thereof being substituted by alanine.

22. The modified P450 monooxygenase according to claim 1, wherein at least one amino acid of SEQ ID NO.: 1 selected from the group consisting of leucine 87, glutamic acid 88, lysine 89, isoleucine 90, threonine 91, proline 92, valine 93, serine 94,threonine 98, threonine 100, leucine 101, arginine 103, tyrosine 104, aspartic acid 105, histidine 196, threonine 197, valine 198, asparagine 199, threonine 200, tryptophan 201, glycine 202, arginine 203, proline 204, proline 206, glutamic acid 207, glutamic acid 208, glutamine 209, and valine 210 is substituted by alanine.

* * * * *